US011530995B2

(12) United States Patent
Green et al.

(10) Patent No.: US 11,530,995 B2
(45) Date of Patent: Dec. 20, 2022

(54) MINI C-ARM IMAGING SYSTEM WITH STEPLESS COLLIMATION

(71) Applicant: OrthoScan, Inc., Scottsdale, AZ (US)

(72) Inventors: Andy Webster Green, Scottsdale, AZ (US); Kyle Ray Simonsen, Apache Junction, AZ (US)

(73) Assignee: OrthoScan, Inc., Scottsdale, AZ (US)

( * ) Notice: Subject to any disclaimer, the term of this patent is extended or adjusted under 35 U.S.C. 154(b) by 0 days.

(21) Appl. No.: 17/018,331

(22) Filed: Sep. 11, 2020

(65) Prior Publication Data

US 2021/0096088 A1 Apr. 1, 2021

Related U.S. Application Data

(60) Provisional application No. 62/899,627, filed on Sep. 12, 2019.

(51) Int. Cl.
*A61B 6/06* (2006.01)
*G01N 23/04* (2018.01)
*G21K 1/02* (2006.01)
*A61B 6/00* (2006.01)

(52) U.S. Cl.
CPC ............ *G01N 23/043* (2013.01); *A61B 6/06* (2013.01); *A61B 6/4405* (2013.01); *A61B 6/4441* (2013.01); *A61B 6/4476* (2013.01); *A61B 6/487* (2013.01); *G21K 1/02* (2013.01); *G01N 2223/301* (2013.01); *G01N 2223/316* (2013.01); *G01N 2223/32* (2013.01); *G01N 2223/406* (2013.01)

(58) Field of Classification Search
CPC ...... G01N 23/00; G01N 23/04; G01N 23/043; G01N 2223/32; G01N 2223/301; G01N 2223/316; G01N 2223/406; G21K 1/02; G21K 1/04; A61B 6/00; A61B 6/06; A61B 6/4405; A61B 6/4441; A61B 6/487; A61B 6/4476
See application file for complete search history.

(56) References Cited

U.S. PATENT DOCUMENTS

| 4,203,037 A | 5/1980 | Gur et al. |
| 4,380,820 A | 4/1983 | Cutter |
| 4,489,426 A | 12/1984 | Grass et al. |
| 4,618,980 A | 10/1986 | Lescrenier et al. |
| 5,396,534 A | 3/1995 | Thomas |
| 5,757,881 A | 5/1998 | Hughes |
| 7,583,788 B2 | 9/2009 | Zheng et al. |

(Continued)

FOREIGN PATENT DOCUMENTS

GB 2170380 7/1986

OTHER PUBLICATIONS

International Search Report and Written Opinion dated Jan. 8, 2021 in Application No. PCT/US2020/050531, filed Sep. 11, 2020.

*Primary Examiner* — Jurie Yun
(74) *Attorney, Agent, or Firm* — Knobbe Martens Olson & Bear, LLP (57) ABSTRACT

The disclosure relates to a Mobile Fluoroscopic Device consisting of a Mini-C Arm assembly containing a stepless collimating apparatus which is adjustable using pairs of linear translating, opaque to x-ray plates (2). Each pair of plates are operated by a drive mechanism including a motor (3), gears (4, 6), and racks (5) making it possible to increase or decrease the cross-sectional area of the x-ray beam relative to the x-ray sensor surface area.

16 Claims, 5 Drawing Sheets

(56) References Cited

U.S. PATENT DOCUMENTS

| | | |
|---|---|---|
| 9,161,727 B2 | 10/2015 | Jenkins et al. |
| 9,192,343 B2 | 11/2015 | Eklund |
| 9,554,757 B2 | 1/2017 | Steinhauser |
| 9,785,246 B2 | 10/2017 | Isaacs et al. |
| 9,872,659 B2 | 1/2018 | Jenkins et al. |
| 9,962,134 B2 | 5/2018 | Brody |
| 2015/0313558 A1 | 11/2015 | Melman et al. |
| 2017/0186507 A1 | 6/2017 | Kang et al. |
| 2017/0188985 A1 | 7/2017 | Brudniok |
| 2017/0273645 A1 | 9/2017 | Raupach et al. |
| 2018/0070910 A1 | 3/2018 | Franklin et al. |
| 2018/0206806 A1 | 7/2018 | Jenkins et al. |
| 2018/0211363 A1 | 7/2018 | Abe et al. |
| 2018/0279981 A1 | 10/2018 | Fehre et al. |
| 2018/0308218 A1 | 10/2018 | Ji et al. |
| 2018/0353146 A1 | 12/2018 | Grondin et al. |
| 2019/0029629 A1 | 1/2019 | Johnson et al. |

MINI C-ARM IMAGING SYSTEM WITH STEPLESS COLLIMATION

PRIORITY CLAIM

This application claims the benefit under 35 U.S.C. 119(e) to U.S. Prov. App. No. 62/899,627 filed on Sep. 12, 2019, which is hereby incorporated by reference in its entirety.

BACKGROUND

Field of the Invention

This disclosure relates in some aspects to a mini C-arm fluoroscopic/radiographic imaging device that includes a motorized stepless collimating apparatus for limiting an x-ray beam during imaging.

SUMMARY

It may be desirable to reduce the exposure area of the X-ray beam during fluoroscopy operation. Adjusting the area may be used to isolate an area of interest and reduce the amount of exposure to non-areas of interest.

In some embodiments, the mini C-arm fluoroscopic/radiographic imaging devices disclosed herein can accommodate the physical constraints of the x-ray "source to image distance" (SID) FDA requirements of Mini-C Arm fluoroscopy devices. The mini C-arm fluoroscopic/radiographic imaging devices disclosed herein can be used in conjunction with image receptors that are both less than and greater than 300 square centimeters. In some embodiments, the mini C-arm fluoroscopic/radiographic imaging devices disclosed herein can be used in conjunction with image receptors that have an area of about 100 square centimeters, about 200 square centimeters, about 300 square centimeters, about 400 square centimeters, about 500 square centimeters, about 600 square centimeters, less than 100 square centimeters, less than 200 square centimeters, less than 300 square centimeters, less than 400 square centimeters, less than 500 square centimeters, less than 600 square centimeters, greater than 100 square centimeters, greater than 200 square centimeters, greater than 300 square centimeters, greater than 400 square centimeters, greater than 500 square centimeters, greater than 600 square centimeters, or any range of the foregoing values.

In some embodiments, a mobile mini C-arm fluoroscopic/radiographic imaging device includes an x-ray beam generator. In some embodiments, a mobile mini C-arm fluoroscopic/radiographic imaging device includes an image receptor. In some embodiments, a mobile mini C-arm fluoroscopic/radiographic imaging device includes a curved structural support assembly. In some embodiments, a mobile mini C-arm fluoroscopic/radiographic imaging device includes a collimating apparatus. The collimating apparatus can allow for user-controlled stepless adjustment of the x-ray beam size through a continuous range to optimize the field of view at the image receptor. The collimating apparatus can allow for user-controlled stepless adjustment of the x-ray beam shape through a continuous range to optimize the field of view at the image receptor. The collimating apparatus can allow for user-controlled stepless adjustment of the x-ray beam size and shape through a continuous range to optimize the field of view at the image receptor. The collimating apparatus can allow for user-controlled stepless adjustment as described herein.

In some embodiments, the collimating apparatus can include a plurality of movable plates. The movable plates can be coupled to racks. The racks can be configured to facilitate translation along linear rails.

In some embodiments, the collimating apparatus comprises one or more drive gears. The one or more drive gears can be configured to move the plurality of movable plates with respect to each other. In some embodiments, one drive gear moves one of the movable plates. In some embodiments, one drive gear moves two of the movable plates. In some embodiments, one drive gear moves two of the movable plates in opposite directions. The collimating apparatus can allow for user-controlled stepless adjustment by moving the movable plates by rotating the drive gears. The drive gears can interact with the racks coupled to the movable plates.

In some embodiments, the collimating apparatus can include one or more idle gears. The one or more idle gears can facilitate the movement the plurality of movable plates with respect to each other. The one or more idle gears can transmit rotation, but does not drive the motion. The one or more idle gears can change the direction of the motion. The one or more idle gears can transmit rotation along a distance.

In some embodiments, the collimating apparatus can include one or more motors. The one or more motors can drive the drive gears to move the plurality of movable plates with respect to each other. The motor can be directly connected to the drive gear. The motor can be indirectly connected to the drive gear. The motor can drive a single drive gear. The motor can drive one or more drive gears.

In some embodiments, the one or more motors can be positioned above the collimating apparatus. In some embodiments, the one or more motors can be positioned below the collimating apparatus. In some embodiments, the one or more motors can be positioned relative to the collimating apparatus in use.

In some embodiments, the plurality of moveable plates can include any number of plates. The plurality of moveable plates can include a first pair of plates. The first pair of plates can be horizontal in use. The first pair of plates can be parallel in use. In some embodiments, the first pair of plates can be coupled to a first drive gear. The rotation of the first drive gear can result in the first pair of plates moving closer together or farther apart from each other depending on the direction of rotation of the first drive gear. The plurality of moveable plates can include a second pair of plates. The second pair of plates can be horizontal in use. The second pair of plates can be parallel in use. The first pair of plates and the second pair of plates can be perpendicular to each other. In some embodiments, the second pair of plates can be coupled to a second drive gear. The rotation of the second drive gear can result in the second pair of plates moving closer together or farther apart from each other depending on the direction of rotation of the first drive gear. In use, rotation of the drive gears can result in the first pair of plates moving closer together or farther apart from each other and/or the second pair of plates moving closer together or farther part from each other.

In some embodiments, the plurality of moveable plates are configured to create an x-ray field that is 400 cm². In some embodiments, the plurality of moveable plates are configured to create an x-ray field having an area of about 100 square centimeters, about 200 square centimeters, about 300 square centimeters, about 400 square centimeters, about 500 square centimeters, about 600 square centimeters, less than 100 square centimeters, less than 200 square centimeters, less than 300 square centimeters, less than 400 square centimeters, less than 500 square centimeters, less than 600 square centimeters, greater than 100 square centimeters, greater than 200 square centimeters, greater than 300 square centimeters, greater than 400 square centimeters, greater than 500 square centimeters, greater than 600 square centimeters, or any range of the foregoing values.

In some embodiments, the plurality of moveable plates are configured to close, impeding the x-ray beam. The first pair of plates can be brought together to close. The first pair of plates can abut. The second pair of plates can be brought together to close. The second pair of plates can abut. In some embodiments, only one pair of plates close. In some embodiments, both pairs of plates close.

In some embodiments, the a mobile mini C-arm fluoroscopic/radiographic imaging device can include a x-ray beam generator. In some embodiments, a mobile mini C-arm fluoroscopic/radiographic imaging device can include an image receptor. In some embodiments, a mobile mini C-arm fluoroscopic/radiographic imaging device can include a structural support assembly. In some embodiments, a mobile mini C-arm fluoroscopic/radiographic imaging device can include a collimating apparatus. The collimating apparatus can be configured to allow for user-controlled stepless adjustment of the x-ray beam size and shape through a continuous range to enhance (which can include increasing and/or decreasing) the field of view at the image receptor.

In some embodiments, a mobile mini C-arm fluoroscopic/radiographic imaging device is provided. The mobile mini C-arm fluoroscopic/radiographic imaging device can include a x-ray beam generator, an image receptor, a curved structural support assembly, and a collimating apparatus configured to allow for user-controlled stepless adjustment of the x-ray beam size and shape through a continuous range to optimize the field of view at the image receptor.

In some embodiments, the collimating apparatus comprises a plurality of movable plates coupled to racks configured to facilitate translation along linear rails. In some embodiments, the collimating apparatus comprises drive gears configured to move the plurality of movable plates with respect to each other. In some embodiments, the collimating apparatus further comprises idle gears configured to move the plurality of movable plates with respect to each other. In some embodiments, the collimating apparatus further comprises one or more motors configured to drive the drive gears to move the plurality of movable plates with respect to each other. In some embodiments, the one or more motors are positioned above the collimating apparatus. In some embodiments, the plurality of moveable plates comprises a first pair of plates and a second pair of plates, wherein rotation of the drive gears results in the first pair of plates moving closer together or farther apart from each other and/or the second pair of plates moving closer together or farther part from each other. In some embodiments, the plurality of moveable plates are configured to create an x-ray field that is 400 cm². In some embodiments, the plurality of moveable plates are configured to close, impeding the x-ray beam.

In some embodiments, a mobile mini C-arm fluoroscopic/radiographic imaging device is provided. The mobile mini C-arm fluoroscopic/radiographic imaging device can include a x-ray beam generator, an image receptor, a structural support assembly, and a collimating apparatus configured to allow for user-controlled stepless adjustment of the x-ray beam size and shape through a continuous range to enhance the field of view at the image receptor. In some embodiments, the imaging device further comprises the features described herein.

In some embodiments, a mobile mini C-arm fluoroscopic/radiographic imaging device is provided. The mobile mini C-arm fluoroscopic/radiographic imaging device can include a x-ray beam generator, an image receptor, a support assembly, and a collimating apparatus configured to allow for user-controlled stepless adjustment of the x-ray beam size and shape through a continuous range to optimize the field of view at the image receptor. In some embodiments, the collimating apparatus comprises a first pair of plates and a second pair of plates.

In some embodiments, the imaging device further comprises a first drive gear configured to translate a plate of the first pair of plates. In some embodiments, the imaging device further comprises a first idle gear configured to translate another plate of the first pair of plates. In some embodiments, the first drive gear and the first idle gear bring the first pair of plates toward each other. In some embodiments, the imaging device further comprises a second drive gear configured to translate a plate of the second pair of plates. In some embodiments, the imaging device further comprises a second idle gear configured to translate another plate of the second pair of plates. In some embodiments, the second drive gear and the second idle gear bring the second pair of plates toward each other. In some embodiments, the first pair of plates and the second pair of plates are perpendicular. In some embodiments, the imaging device further comprises a first motor and a second motor, wherein the first motor and the second motor are positioned above the collimating apparatus in use. In some embodiments, the first pair of plates move closer together or farther apart from each other and the second pair of plates move closer together or farther part from each other independent of the movement of the first pair of plates. In some embodiments, the plurality of moveable plates are configured to create an x-ray field that is 400 cm² or smaller. In some embodiments, the first pair of plates and the second pair of plates are configured to close, impeding the x-ray beam.

In some embodiments, a system or method can comprise, consist essentially of, consist of, or not comprise any number of features of the disclosure.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

Figure 1:
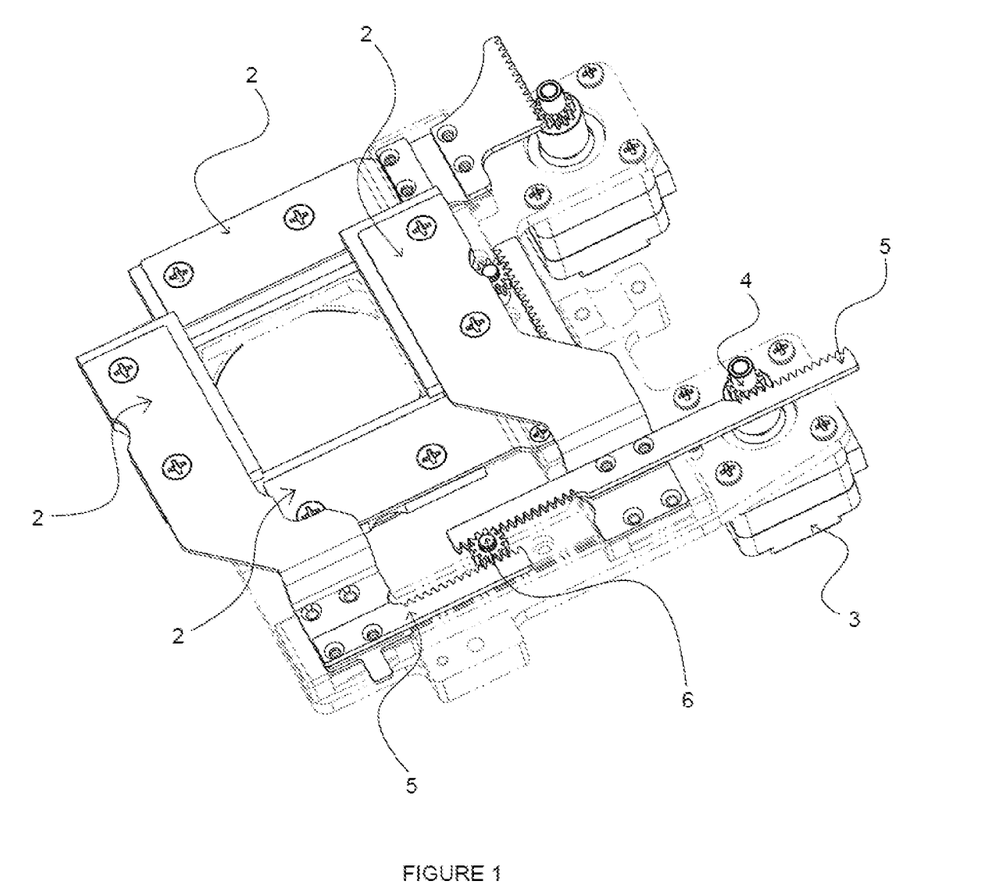
FIG. 1 illustrates an embodiment of a stepless collimating apparatus in detail.

FIG. 1 presents an isometric view of an embodiment of a stepless collimating apparatus (20). The stepless collimating apparatus (20) generally comprising pairs of opaque to x-ray plates (2). The stepless collimating apparatus (20) can include four plates. The stepless collimating apparatus (20) can comprise two sets of plates, a first pair of plates and a second pair of plates. The first pair of plates are shown as generally vertically oriented as shown in FIG. 1. The first pair of plates can be parallel in use. The second pair of plates are shown as generally horizontally oriented as shown in FIG. 1. The second pair of plates can be parallel in use. While four plates are shown, any number of plates are contemplated. While two sets of plates are shown, any number of sets of plates are contemplated.

In some embodiments, the movement of the sets of plates are coupled. The first pair of plates can move toward and away from each other. The first pair of plates can move simultaneously. The second pair of plates can move toward and away from each other. The second pair of plates can move simultaneously. In some embodiments, the movement of the plates within the sets of plates are uncoupled. The plates of the first pair of plates can move independently. The plates of the second pair of plates can move independently. In some embodiments, the pairs of plates can move relative to each other. The first pair of plates and the second pair of plates can move independently of each other. The first pair of plates and the second pair of plates can move simultaneously.

The plates (2) are coupled to racks (5). Each plate (2) can be coupled to a rack (5). The plate (2) and the rack (5) can be separately formed and coupled. The plate (2) and the rack (5) can be integrally formed. The rack (5) can facilitate translation of the plate (2) along linear rails. The plate (2) can be freely slideable along the linear rail when the rack (5) is driven, as described herein.

The stepless collimating apparatus (20) can include one or more motors (3). The motors (3) can be user interface-controlled motors. The motors (3) are assembled or operatively coupled to drive gears (4). The motor (3) can be directly coupled to the drive gear (4). The motor can be indirectly coupled to the drive gear (4). Each motor (3) can drive a single drive gear (4). Each motor (3) can drive two or more drive gears (4). The stepless collimating apparatus (20) can include one or more idle gears (6). The motors (3) are assembled or operatively coupled to drive gears (4) which are used in conjunction with idle gears (6). The idle gears (6) can be spaced apart from the drive gear (4). The idle gear (6) can change the direction of the drive gear (4). The idle gear (6) can facilitate the motion of the plates (2) of a pair of plates toward and away from each other, as described herein. The rack (5) and drive gear (4) can function as a rack and pinion drive system. The rack (5) and drive gear (4) can convert rotational motion of the drive gear (4) to translation of the rack (5). The drive gear (4) can be circular gear. The rack (5) can includes a series of linear gears. Rotating the drive gear (4) causes the rack (5) to be driven linearly. The rack (5) can be laterally maneuverable by the drive gear (4)

The stepless collimating apparatus (20) can allow the plates (2) to open or close in a "limitless" fashion. The stepless collimating apparatus (20) can allow the plates (2) to move from a fully open state to a fully closed state. The stepless collimating apparatus (20) can allow the plates (2) to move back to a fully open state.

Taking the bottom right drive gear (4) in FIG. 1, the motion of the first pair of plates is described. The rotation of the drive gear (4) causes the rack (5) to translate. The rack (5) is coupled to the rightmost plate of the first pair of plates (2). The drive gear (4) acts as a pinon to the rack (5). The drive gear (4) maneuvers a first rack (5) in a first direction. The drive gear (4) translate the first rack (5) generally to the right or left depending on the direction of rotation. The rack (5) coupled to the rightmost plate of the first pair of plates (2) rotates the idle gear (6). The idle gear (6) changes the direction of the rotation. The idle gear (6) contacts a second rack (5) of the leftmost plate of the first pair of plates (2). The idle gear (6) acts as a pinon to the rack (5). The idle gear (6) maneuvers the second rack (5) in a second direction. The rotation of the idle gear (6) causes the second rack (5) to move in a second direction. The second direction is opposite the first direction. The movement of the drive gear (4) and the idle gear (6) results in the first pair of plates (2) moving closer together or farther apart. The movement of the drive gear (4) and the idle gear (6) result in one plate of the first pair of plates moving right and the other plate of the first pair of plates moving left as viewed in FIG. 1.

The second pair of plates can have a similar movement toward and away from each other. The second pair of plates are shown as generally horizontally oriented in FIG. 1. The drive gear (4) is near the upper right corner. The rotation of the drive gear (4) causes a third rack (5) to translate. The third rack (5) is coupled to the uppermost plate of the second pair of plates (2). The drive gear (4) maneuvers the third rack (5) in a third direction. The drive gear (4) translate the third rack (5) generally up or down depending on the direction of rotation. The rack (5) coupled to the uppermost plate of the first pair of plates (2) rotates the idle gear (6). The idle gear (6) changes the direction of the rotation. The idle gear (6) contacts a fourth rack (5) of the bottommost plate of the second pair of plates (2). The idle gear (6) maneuvers the fourth rack (5) in a second direction. The rotation of the idle gear (6) causes the fourth rack (5) to move in a fourth direction. The third direction is opposite the fourth direction. The movement of the drive gear (4) and the idle gear (6) result in a pair of plates (2) moving closer together or farther apart. The movement of the drive gear (4) and the idle gear (6) result in one plate of the second pair of plates moving up and the other plate of the first pair of plates moving down as viewed in FIG. 1. In some embodiments, two motors (3) are provide. In some embodiments, the first pair of plates (2) move independently of the second pair of plates (2).

Phrased differently, the motors (3) can drive the drive gears (4). The motors (3) can cause motion of the pair of plates (2) with the assistance of idle gears (6). The motors (3), the drive gears (4) and the idle gears (6) can to maneuver the two pairs of plates (2) along a continuum of different positions. The motors (3), the drive gears (4) and the idle gears (6) can to maneuver the two pairs of plates (2) closer together and farther apart. The motors (3), the drive gears (4) and the idle gears (6) can to maneuver the two pairs of plates (2) to provide a continuum of x-ray field sizes between a maximum size and a minimum size. Providing a continuum of x-ray field sizes advantageously enables the x-ray field size to be one of a limitless number of possibilities between the maximum and minimum sizes. Providing a continuum of x-ray field sizes advantageously allows more flexibility and user options compared to a stepped or discrete system that has limited numbers or discrete x-ray field sizes.

The stepless collimating apparatus (20) described herein can maneuver the plates (2) to create an enlarged x-ray field. In some embodiments, the stepless collimating apparatus (20) can maneuver the plates (2) to create an enlarged x-ray field, which can be a maximum size, that is 20 cm by 20 cm—providing 400 $cm^2$. In some embodiments, the stepless collimating apparatus (20) can create an enlarged x-ray field having a maximum size of 100 square centimeters, maximum size of 200 square centimeters, maximum size of 300 square centimeters, maximum size of 400 square centimeters, maximum size of 500 square centimeters, maximum size of 600 square centimeters, less than 100 square centimeters, less than 200 square centimeters, less than 300 square centimeters, less than 400 square centimeters, less than 500 square centimeters, less than 600 square centimeters, greater than 100 square centimeters, greater than 200 square centimeters, greater than 300 square centimeters, greater than 400 square centimeters, greater than 500 square centimeters, greater than 600 square centimeters, or any range of the foregoing values. In some aspects, the plates (2) can be maneuvered to create an enlarged x-ray filed that is larger or smaller than 400 cm². The stepless collimating apparatus (20) described herein can maneuver the plates (2) to create a closed x-ray field, which can be the minimum size, that is 0 cm by 0 cm—fully closing the plates (2). The stepless collimating apparatus (20) described herein can maneuver the plates (2) to create x-ray files of varying sizes between a maximum and minimum, which can include x-ray field sizes between 0 cm² and 400 cm². In some embodiments, the stepless collimating apparatus (20) can create an enlarged x-ray field having a range of 0-100 square centimeters, range of 0-200 square centimeters, range of 0-300 square centimeters, range of 0-400 square centimeters, range of 0-500 square centimeters, range of 0-600 square centimeters, or any range of the foregoing vales. In some aspects, the plates (2) can be actuated with motors (3). In some aspects, the plates (2) can be actuated with motorized lead screw steppers. In some aspects, the plates (2) can be actuated with any mechanical means to effectuate linear actuation. In some aspects, the plates (2) can be actuated any type of electric motor, brushless motors, brushed motors, direct drive motors, linear drive motors, servo motors, stepper motors, or combined with another actuation technique described herein.

Figure 2:
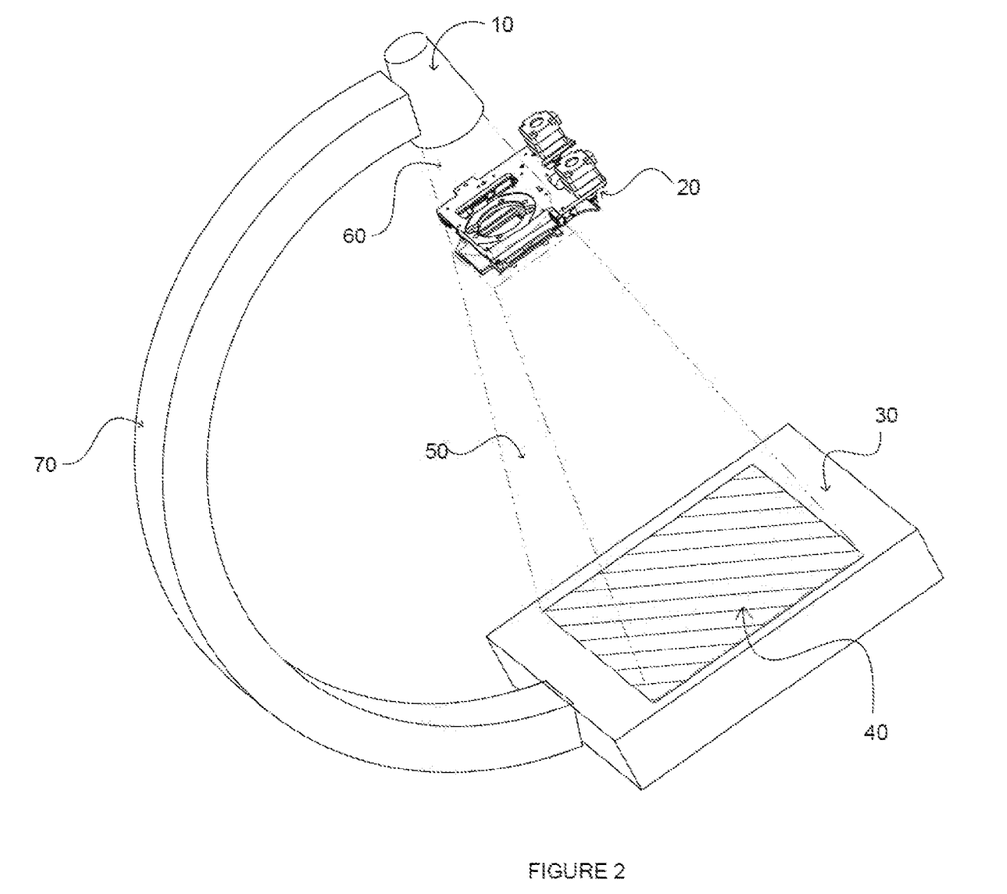
FIG. 2 illustrates an example of a mini C-arm imaging device including a stepless collimating apparatus in an enlarged field state.

FIG. 2 presents an isometric view of a mini C-arm assembly. The mini C-arm assembly can include a curved structural support assembly (70). The mini C-arm assembly can include an x-ray beam generator (10). The mini C-arm assembly can include the stepless collimating device (20), described herein. The mini C-arm assembly can include an image receptor (30). The curved structural support assembly (70) can provide parallel attachment of the x-ray beam generator (10), the stepless collimating device (20), and the image receptor (30). The x-ray beam generator (10) can be positioned above the stepless collimating device (20) which is positioned above the image receptor (30). The stepless collimating device (20) can be horizontal in use. The image receptor (30) can be horizontal in use. In some embodiments, the x-ray beam generator (10) and image receptor (30) are fixedly attached or otherwise coupled to both ends of the curved structural support assembly (70). The curved structural support assembly (70) can take the form of a C or a U in some embodiments. In some embodiments, the x-ray beam generator (10) and image receptor (30) are attached to movable extensions of the curved structural support assembly (70). The mini C-arm assembly can also incorporate features of arm assemblies and articulating arms operably connected to the mini C-arm assembly as disclosed, for example, in U.S. Pat. No. 8,708,561 to Eaves, which is hereby incorporated by reference in its entirety. During operation, the x-ray beam (60) produced by the x-ray beam generator (10) passes through the stepless collimating apparatus (20). As illustrated, the stepless collimating apparatus (20) is in an enlarged open state or fully open state. As the x-ray beam (60) exits the stepless collimating apparatus (20), the beam shape (50) is adjusted to produce the enlarged or maximum detector field size (40).

The detector field size (40) is dependent on the position of the pairs of plates (2). The pairs of plates (2) can be brought together to make the detector field size (40) smaller. The pairs of plates (2) can be moved apart to make the detector field size (40) larger. The first pairs of plates (2) can be moved to change the detector field size in the right-left direction when viewed in FIG. 1. The second pairs of plates (2) can be moved to change the detector field size in the up-down direction when viewed in FIG. 1. The pairs of plates (2) can change the detector field size to an infinite number of sizes or surface areas. The beam shape (50) is dependent on the position of the pairs of plates (2). The first pairs of plates (2) can be moved to change the beam shape in the right-left direction when viewed in FIG. 1. The second pairs of plates (2) can be moved to change the beam shape in the up-down direction when viewed in FIG. 1. The pairs of plates (2) can change the beam shape from square to an indefinite number of rectangular shapes. The pairs of plates (2) can change the polygonal shape of the beam shape (50).

In some embodiments, the stepless collimating device (20) can have a reduced thickness or height. In some embodiments, mounting the motors (3) above, on top of, and/or upon the collimating apparatus (20) can reduce the overall thickness or height. In some embodiments, utilization of the racks (5), idle gears (6), and/or drive gears (4) can reduce the overall thickness or height. In some embodiments, the stepless collimating device (20) can have a reduced thickness or height by reducing the overall thickness or height by the size of the motors (3). In some embodiments, the motors (3) are mounted on an upper portion. This can allow an overall thickness or height that is less compared to a design implementing motors that actuate in a linear manner. The reduced thickness or height can advantageously facilitate an improved useful distance between the x-ray generator (10) and the image receptor (30). This can be accomplished while maintaining the regulatory distance requirement between the x-ray beam generator (10) and one or more of the underside of the stepless collimating apparatus (20), exit of the stepless collimating apparatus (20), and/or point, position, and/or location at which the x-ray beam exits the stepless collimating apparatus (20). For example, there is a regulatory minimum distance between the x-ray beam generator (10) and the point, position, and/or location at which the x-ray beam exits the collimating apparatus (20). Accordingly, the stepless collimating apparatus (20) can meet the minimum regulatory distance between the x-ray beam generator (10) and the point, position, and/or location at which the x-ray beam exits the collimating apparatus (20), while increasing or improving the useful or operable distance between the point, position, and/or location at which the x-ray beam exits the collimating apparatus (20) and the image receptor (30) due to the reduced thickness or height.

Figure 2B:
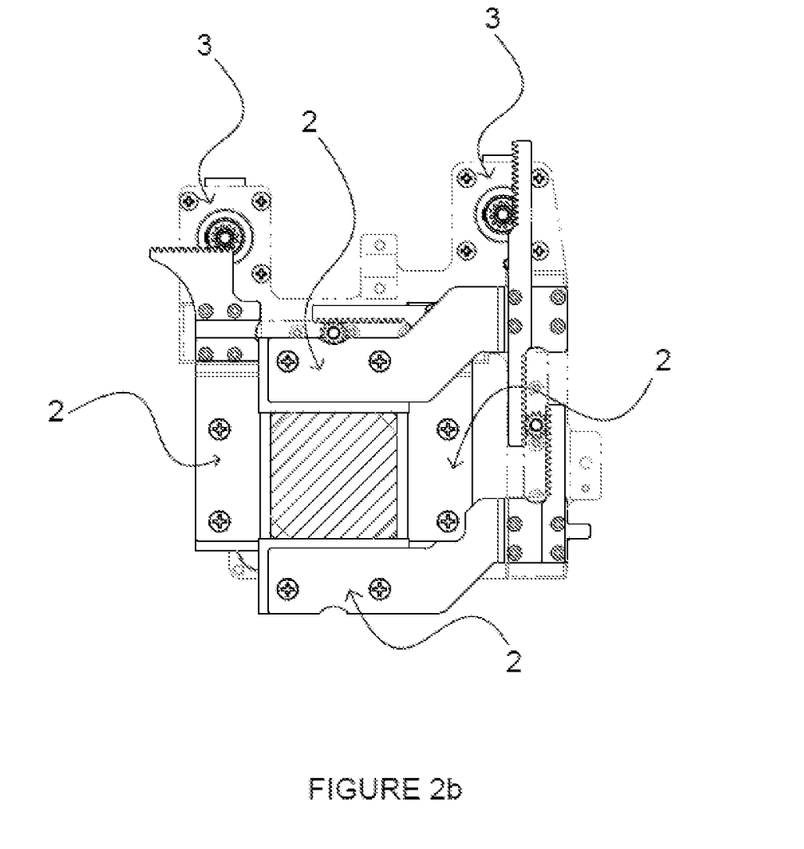
FIG. 2b illustrates the details of the stepless collimating apparatus in the enlarged field state.

FIG. 2b presents a bottom view of the stepless collimating apparatus (20). As illustrated, the stepless collimating apparatus (20) is in an enlarged or fully open state with each pair of opaque to x-ray plates (2) having been moved to an outer or outermost extents via the user interface-controlled motors (3). The two motors (3) are shown which drive the drive gears (4). One motor drives the first pair of plates (2) and the other motor drive the second pair of plates (2). The racks (5) are shown coupled to their respective plate (2). The racks (5) can have any elongated shape. The racks (5) can include a set of gears. The drive gear (4) acts as a pinion and causes translation of the racks (5) as the drive gear (4) rotates. The pairs of plates (2) can be mounted on the collimating apparatus (20). The pairs of plates (2) can be mounted on one or more rails. The rails allow low friction sliding of the pair of plates (2) to facilitate movement by the drive gears (4). The two plates of the first pair of plates (2) are diametrically opposed. The two plates of the first pair of plates (2) are generally parallel. The two plates of the first pair of plates (2) can move toward each other by equal amounts. The two plates of the second pair of plates (2) are diametrically opposed. The two plates of the second pair of plates (2) are generally parallel. The two plates of the second pair of plates (2) can move toward each other by equal amounts. The first pair of plates (2) can be positioned above the second pair of plates (2) as shown in FIG. 1. The second pair of plates (2) can be positioned below the first pair of plates (2) as shown in FIG. 2b. The pairs of plates (2) can be positioned to avoid interference during motion of the plates (2). The stepless collimating apparatus (20) is generally horizontal in use. The pairs of blades (2) have a stacked configuration. The pair of blades (2) have a low profile configuration. One pair of blades is over another pair of blades.

Figure 3:
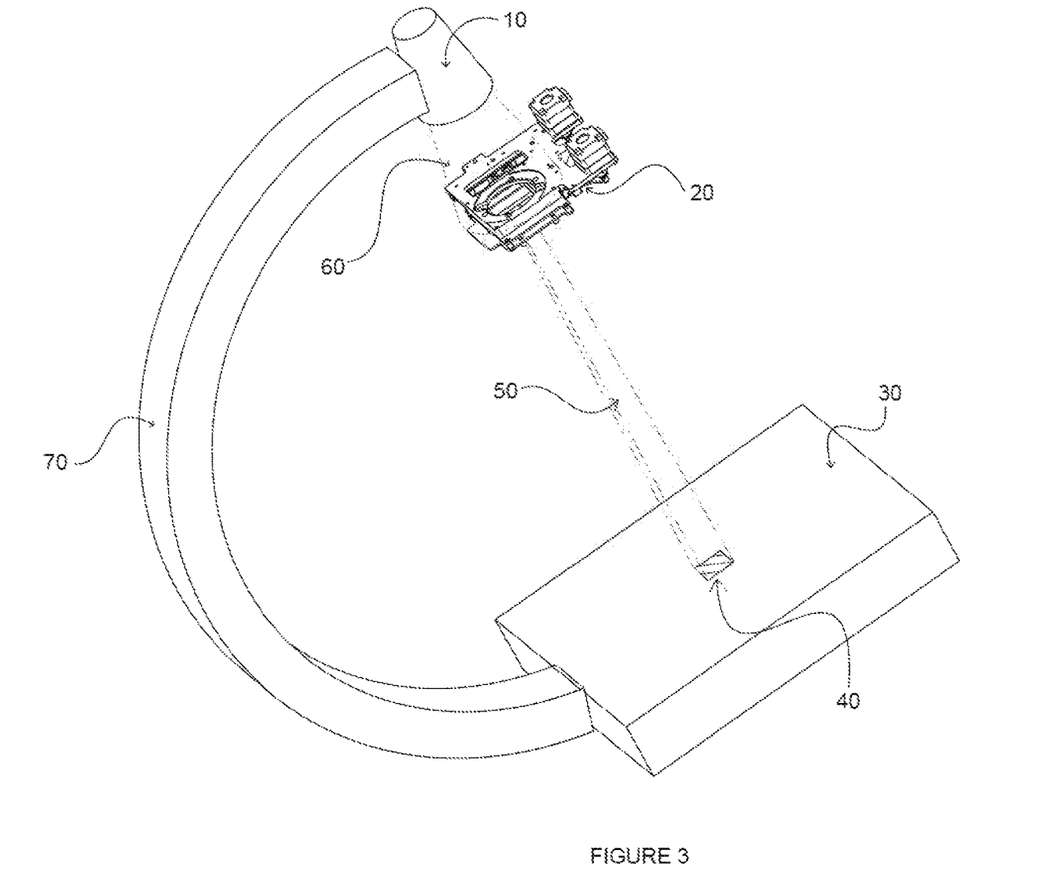
FIG. 3 illustrates an example of a mini C-arm imaging device including the stepless collimating apparatus in the reduced field state, which can be about or less than about 5 cm×5 cm.

FIG. 3 presents an isometric view of the mini C-arm assembly of FIG. 2. As illustrated, the stepless collimating apparatus (20) is in a reduced or minimally open state. As the x-ray beam exits the stepless collimating apparatus (20), the beam shape (50) is adjusted to the reduced or minimum detector field size (40). The detector field size (40) is dependent on the position of the pairs of plates (2). Comparing FIG. 2 and FIG. 3, the pairs of plates (2) can be brought together to make the detector field size (40) smaller as shown in FIG. 3. The first pairs of plates (2) can be moved to change the detector field size in the right-left direction when the stepless collimating apparatus (20) is viewed as shown in FIG. 1. The second pairs of plates (2) can be moved to change the detector field size in the up-down direction when the stepless collimating apparatus (20) is viewed as shown in FIG. 1. The first pairs of plates (2) can be moved to change the beam shape and size in the right-left direction when the stepless collimating apparatus (20) is viewed as shown in FIG. 1. The second pairs of plates (2) can be moved to change the beam shape and size in the up-down direction when the stepless collimating apparatus (20) is viewed as shown in FIG. 1.

Figure 3B:
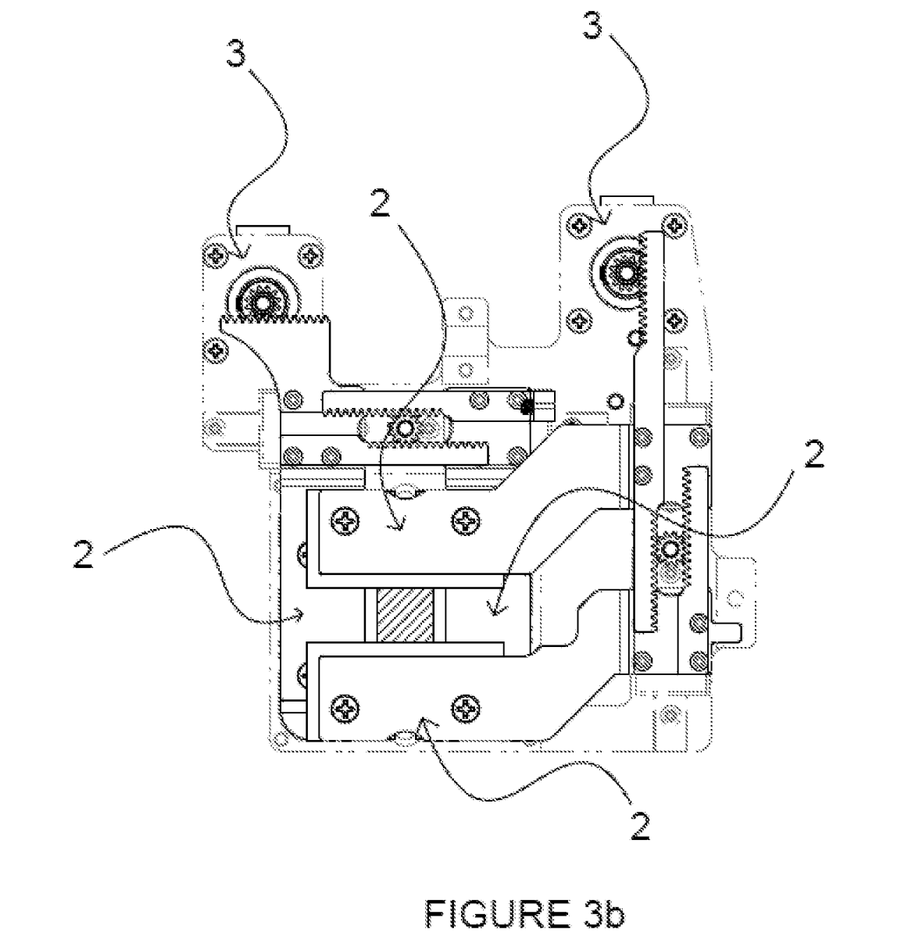
FIG. 3b illustrates the details of an embodiment of the stepless collimating apparatus in a reduced field state.

FIG. 3b presents a bottom view of the stepless collimating apparatus (20). As illustrated, the stepless collimating apparatus (20) is in a reduced or minimally open state with each pair of opaque to x-ray plates (2) having been moved to their inner or innermost extents via the user interface-controlled motors (3). Comparing FIG. 2b and FIG. 3b, the pairs of plates (2) can be brought together. The first pairs of plates (2) can be moved to in the right-left direction when the stepless collimating apparatus (20) is viewed as shown in FIG. 1. The second pairs of plates (2) can be moved in the up-down direction when the stepless collimating apparatus (20) is viewed as shown in FIG. 1. The first pairs of plates (2) can be moved to change the beam shape and size in the right-left direction. The second pairs of plates (2) can be moved to change the beam shape and size in the up-down direction. The polygonal shape of the beam shape (50) has changed between FIGS. 2b and 3b, e.g., from a larger square or rectangle to a smaller square or rectangle. The detector field size has changed from a larger surface area to a smaller surface area. In some adjustments, only the right-left direction is changed by bringing the first pair of plates (2) toward or away from each other. In some adjustments, only the up-down direction is changed by bringing the second pair of plates (2) toward or away from each other. In some embodiments, both pairs of plates (2) are moved. In some embodiments, both pairs of plates (2) are moved to make the beam size or shape smaller. In some embodiments, both pairs of plates (2) are moved to make the beam size or shape larger. In some embodiments, both pairs of plates (2) are moved to change the beam shape and size.

The stepless collimating apparatus can be further adjusted. The first pair of plates (2) can contact each other. The second pair of plates can contact each other. The pairs of plates (2) can be positioned to prevent the x-ray beam (60) produced by the x-ray beam generator (10) from passing through the stepless collimating apparatus (20). The pairs of plates (2) can be positioned such that there is no beam shape (50). The pairs of plates (2) can be positioned such that there is no detector field size (40). The pairs of plates (2) can be closed. The stepless collimating apparatus can be adjusted from any open position to the closed position. The stepless collimating apparatus can be adjusted from the closed position to any open position upon movement of the pair of plates.

In some embodiments, the mini imaging apparatus may comprise any suitable x-ray capture technology. In some embodiments, the mini imaging apparatus comprises an image intensifier. The image intensifier may be configured to amplify diagnostic x-rays to create an output image of an anatomy, such as for example a hand, a knee, and the like. In some embodiments, the mini imaging apparatus may comprise a flat panel detector. The flat panel detector may be any sensor for detecting x-rays and capturing a diagnostic image, now known or hereinafter devised. The flat panel detector may be of any suitable type, including amorphous silicon detectors, amorphous selenium detectors, and plasma based detectors. In some embodiments, the flat panel detector is configured capture x-ray emitted from an x-ray source, which are converted to a digital image(s) or digital video. In some embodiments, the image intensifier or flat panel detector can be employed in mini-imaging systems to provide lower doses of radiation to a patient.

In some embodiments, one or more systems and electrical subsystems contained therein can be operated by a foot-switch control, a series of controls located on the outer housing of the x-ray source, a keyboard associated therewith, and/or any user input. The electrical subsystems can be contained within a body portion. An image receptor, such as for example an image intensifier and/or a flat panel detector, receives photons from an x-ray source, by any method or system now known or hereinafter devised. The image receptor converts the x-ray to a manipulatable electrical signal that is transmitted to an image processing unit. The image processing unit may be any hardware and/or software system, now know or hereinafter devised, configured to receive an electrical signal and convert the signal into an image. In some embodiments, the image processing unit interprets the electrical signals from the image receptor and is able to produce a high-resolution moving image and display the moving image on a monitor. The image processing unit can be configured to manipulate the image by one or more of the following: removing noise from the image; reducing motion-blur through the averaging multiple frames; rotating the image clockwise or counterclockwise; and/or increasing or decreasing image brightness and contrast. The image processing unit can be configured to provide automatic control to x-ray source. The image processing unit can be configured to record the post-processed image to a printer, directly to remote workstation(s) or storage server(s) via industry standard electronic communications protocols, or via an externally connected solid state media device.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "actuating plates of a stepless collimator" includes "instructing the actuating of plates of a stepless collimator." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A mobile mini C-arm fluoroscopic/radiographic imaging device comprising:
   a x-ray beam generator;
   an image receptor;
   a curved structural support assembly; and
   a collimating apparatus configured to allow for user-controlled stepless adjustment of an x-ray beam size and shape through a continuous range to optimize a field of view at the image receptor, the collimating apparatus comprising:
      a first pair of plates, each of the first pair of plates coupled to a first rack;
      a second pair of plates, each of the second pair of plates coupled to a second rack;
      a first drive gear configured to interface with the first rack coupled to one of the first pair of plates and to rotate to linearly translate the first rack coupled to the one of the first pair of plates;
      a second drive gear configured to interface with the second rack coupled to one of the second pair of plates and to rotate to linearly translate the second rack coupled to the one of the second pair of plates;
      a first idler gear configured to interface with both the first rack coupled to the one of the first pair of plates and the first rack coupled to the other of the first pair of plates, wherein the translation of the first rack coupled to the one of the first pair of plates causes the first idler gear to rotate which, in turn, causes the first rack coupled to the other of the first pair of plates to translate such that the first pair of plates move closer together or farther apart from each other; and
      a second idler gear configured to interface with both the second rack coupled to the one of the second pair of plates and the second rack coupled to the other of the second pair of plates, wherein the translation of the second rack coupled to the one of the second pair of plates causes the second idler gear to rotate which, in turn, causes the second rack coupled to the other of the second pair of plates to translate such that the second pair of plates move closer together or farther apart from each other.

2. The imaging device of claim 1, wherein the first pair of plates and the second pair of plates are configured to translate along linear rails.

3. The imaging device of claim 1, further comprising one or more motors configured to drive the first and the second drive gears.

4. The imaging device of claim 3, wherein the one or more motors are positioned above the collimating apparatus.

5. The imaging device of claim 1, wherein the first pair and the second pair of plates are configured to create an x-ray field that is 400 cm$^2$.

6. The imaging device of claim 1, wherein the first pair and the second pair of plates are configured to close, impeding the x-ray beam.

7. A mobile mini C-arm fluoroscopic/radiographic imaging device comprising:
   a x-ray beam generator;
   an image receptor;
   a structural support assembly; and
   a collimating apparatus configured to allow for user-controlled stepless adjustment of an x-ray beam size and shape through a continuous range to enhance a field of view at the image receptor, the collimating apparatus comprising:
      a first pair of plates, each of the first pair of plates coupled to a first rack;
      a first drive gear configured to interface with the first rack coupled to one of the first pair of plates and to rotate to linearly translate the first rack coupled to the one of the first pair of plates; and
      a first idler gear configured to interface with both the first rack coupled to the one of the first pair of plates and the first rack coupled to the other of the first pair of plates, wherein the translation of the first rack coupled to the one of the first pair of plates causes the first idler gear to rotate which, in turn, causes the first rack coupled to the other of the first pair of plates to translate such that the first pair of plates move closer together or farther apart from each other.

8. A mobile mini C-arm fluoroscopic/radiographic imaging device comprising:

a x-ray beam generator;
an image receptor;
an arm assembly; and
a collimating apparatus configured to allow for user-controlled stepless adjustment of an x-ray beam size and shape through a continuous range to alter a field of view at the image receptor, the collimating apparatus comprising:
  a first pair of plates, each of the first pair of plates coupled to a first rack;
  a first drive gear configured to interface with the first rack coupled to one of the first pair of plates and to rotate to linearly translate the first rack coupled to the one of the first pair of plates; and
  a first idler gear configured to interface with both the first rack coupled to the one of the first pair of plates and the first rack coupled to the other of the first pair of plates, wherein the translation of the first rack coupled to the one of the first pair of plates causes the first idler gear to rotate which, in turn, causes the first rack coupled to the other of the first pair of plates to translate such that the first pair of plates move closer together or farther apart from each other.

9. The imaging device of claim 8, further comprising a second pair of plates, each of the second pair of plates coupled to a second rack.

10. The imaging device of claim 9, further comprising a second drive gear configured to interface with the second rack coupled to one of the second pair of plates and to rotate to linearly translate the second rack coupled to the one of the second pair of plates.

11. The imaging device of claim 10, further comprising a second idler gear configured to interface with both the second rack coupled to the one of the second pair of plates and the second rack coupled to the other of the second pair of plates, wherein the translation of the second rack coupled to the one of the second pair of plates causes the second idler gear to rotate which, in turn, causes the second rack coupled to the other of the second pair of plates to translate such that the second pair of plates move closer together or farther apart from each other.

12. The imaging device of claim 9, wherein the first pair of plates and the second pair of plates are oriented perpendicularly relative to each other.

13. The imaging device of claim 9, further comprising a first motor and a second motor, wherein the first motor and the second motor are positioned above the collimating apparatus in use.

14. The imaging device of claim 9, wherein the first pair of plates are configured to move closer together or farther apart from each other and the second pair of plates are configured to move closer together or farther part from each other independent of the movement of the first pair of plates.

15. The imaging device of claim 9, wherein the first pair of plates and the second pair of plates are configured to create an x-ray field that is 400 $cm^2$ or smaller.

16. The imaging device of claim 9, wherein the first pair of plates and the second pair of plates are configured to close, impeding the x-ray beam.

\* \* \* \* \*